(12) United States Patent
Markelov et al.

(10) Patent No.: US 6,365,107 B1
(45) Date of Patent: Apr. 2, 2002

(54) HEADSPACE INSTRUMENT

(76) Inventors: Michael Markelov, 7276 Greenfield, Chesterland, OH (US) 44026; Yuri Kazakevich, 400 S. Orange Ave., Newark, NJ (US) 07079

( * ) Notice: Subject to any disclaimer, the term of this patent is extended or adjusted under 35 U.S.C. 154(b) by 0 days.

(21) Appl. No.: 09/577,401

(22) Filed: May 22, 2000

Related U.S. Application Data
(60) Provisional application No. 60/135,559, filed on May 24, 1999.

(51) Int. Cl.[7] .................................................. G01N 7/00
(52) U.S. Cl. ............................ 422/83; 422/63; 422/73; 422/80; 422/68.1; 73/863; 73/863.12; 73/863.02; 73/863.03; 436/181
(58) Field of Search .................... 422/83, 68.1; 73/863, 73/23.37, 37; 436/181

(56) References Cited

U.S. PATENT DOCUMENTS

| | | | | |
|---|---|---|---|---|
| 5,363,707 A | * | 11/1994 | Augenblick et al. | 73/864.84 |
| 5,390,551 A | * | 2/1995 | Carvajal et al. | 73/863 |
| 5,411,707 A | * | 5/1995 | Hiatt | 422/68.1 |
| 5,441,700 A | * | 8/1995 | Markelov | 422/83 |
| 5,693,538 A | * | 12/1997 | Capuano et al. | 436/181 |
| 5,792,423 A | * | 8/1998 | Markelov | 422/83 |
| 5,807,701 A | * | 9/1998 | Payne et al. | 435/34 |
| 5,872,306 A | * | 2/1999 | Arnold | 73/23.37 |
| 5,932,482 A | * | 8/1999 | Markelov | 436/181 |
| 6,205,845 B1 | * | 3/2001 | Dinsmoore et al. | 73/37 |

* cited by examiner

Primary Examiner—Jill Warden
Assistant Examiner—Brian J. Sines
(74) Attorney, Agent, or Firm—Ralph E. Jocke; Christopher L. Parmelee; Walker & Jocke LPA

(57) ABSTRACT

A headspace instrument (10, 70) operates to equilibrate a vapor phase of a headspace sample in a sample loop (40, 74). The sample is equilibrated by flow through the headspace between variable volume chambers (28, 50, 86, 90). The volume of the variable volume chambers are changed in coordinated relation so that a constant total volume is always maintained. An aliquot of the equilibrated sample in the sample loop is delivered to an analytical instrument. The headspace instrument enables delivering a vapor sample from a headspace under conditions which do not disturb the thermodynamic equilibrium between the vapor phase and the non-vapor phase of the sample and avoids having the sampling process impact the results of the analysis. Alternative forms of the headspace instrument enable the conduct of concentration dependent processes and absorption and desorption experiments.

24 Claims, 8 Drawing Sheets

HEADSPACE INSTRUMENT

This application claims the benefit of U.S. Provisional Application No.: 60/135,559 filed May 24, 1999.

TECHNICAL FIELD

This invention relates to devices and methods for chemical analysis of materials. Specifically this invention relates to headspace analysis, and a headspace instrument used to increase sensitivity and repeatability in conducting headspace analysis.

BACKGROUND ART

Headspace analysis is a relatively new technique which enables the sampling of a vapor phase of a sample with an analytical instrument. Headspace sampling ensures that only volatile materials are delivered for analysis. For example when the analytical instrument used is a gas chromatograph, headspace sampling assures that only volatile species that can be eluted from a column of a gas chromatograph will be introduced into the instrument.

In headspace sampling a volatile non-vapor phase of a substance being analyzed, which may be either liquid or solid, attains equilibrium with a vapor phase of the substance within a sealed vial. Equilibrium is established when the non-vapor phase of the substance in the vial no longer changes so that the total quantity of the vapor and non-vapor phases remains constant. Often a syringe is used to retrieve a small sample of the vapor for analysis. The retrieved vapor is then introduced into an analytical instrument. Headspace technology is advantageous over conventional direct sample injection techniques because it allows only vapor to enter the analytical instrument. This is advantageous because it reduces the chance of contamination or damage to the analytical instrument due to introduction of unevaporated sample material. Because the sample is in vapor form, greater sample volumes may be supplied to the instrument. Increased sample size generally results in increased sensitivity.

Samples of headspace vapor may be extracted from a sample vial using a number of other techniques. Such techniques often involve equilibrating the vapor and non-vapor phase of a substance for analysis within a closed vial. A sample needle is moved to pierce a septum bounding the headspace in the vial. As a result a fluid passage through the needle is in fluid communication with the vapor phase of the sample in the headspace. To extract the headspace sample it is usually necessary to first pressurize the headspace with a suitable gas.

After the headspace has been pressurized, the pressure is released allowing the sample material to pass out of the vial and into an analytical instrument or other device for collecting or analyzing the sample. Techniques for extracting headspace vapor from a vial are shown in U.S. Pat. No. 5,441,700 the disclosure of which is incorporated by reference as if fully rewritten herein.

A drawback associated with conventional techniques for the extraction of sample vapor from a headspace vial is that variations in pressure must be achieved to extract the sample material. Such variations in pressure often change the equilibrium conditions between the vapor phase and the non-vapor phase of the substance being analyzed. Changes in equilibrium may change the makeup of the headspace vapor. Such changes which result from the sampling process often impact the results in ways that are undesirable.

Thus there exists a need for a headspace instrument and method of operation which minimizes the effects of the sampling process on the constituents in the sample and which increases sample volumes which may be delivered and/or analyzed by an analytical instrument. There further exists a need for a headspace instrument which may be used to carry out analysis on time or concentration dependent materials.

OBJECTS OF INVENTION

It is an object of the present invention to provide a headspace instrument which achieves the sampling of headspace vapors while minimizing the disturbance of thermodynamic equilibrium.

It is a further object of the present invention to provide a headspace instrument which achieves improved sensitivity.

It is a further object of the present invention to provide a headspace instrument which increases sample volumes which may be analyzed by an analytical instrument.

It is a further object of the present invention to provide a headspace instrument which implements improved sampling methods.

It is a further object of the present invention to provide a headspace instrument which obtains equilibrated samples of headspace vapors under conditions of thermodynamic equilibrium.

It is a further object of the present invention to provide a headspace instrument which reduces the possibility for cross contamination between samples.

It is a further object of the present invention to provide a headspace instrument that may be used to measure time dependent or concentration dependent processes in analyzed samples.

It is a further object of the present invention to provide an improved method of sampling materials for analysis.

It is a further object of the present invention to provide a method of sampling that reduces the effects of pressure changes on a headspace sample.

It is a further object of the present invention to provide a method of sampling that may achieve greater sample size.

It is a further object of the present invention to provide a method of sampling which achieves increased sensitivity.

It is a further object of the present invention to provide a method of sampling under conditions of thermodynamic equilibrium.

Further objects of the present invention will be made apparent in the following Best Modes for Carrying Out Invention and the appended claims.

The foregoing objects are accomplished in an exemplary embodiment of the present invention by headspace instrument which handles a vial holding a vapor and a non-vapor phase of a substance for analysis. A first sample needle extends into the headspace in the vial which holds a vapor phase of the substance. The first needle is in fluid connection with a first variable volume chamber. A second sample needle extends in the vapor phase of the substance in the headspace of the vial as well. The second sample needle is in fluid communication with a sample loop and a second variable volume chamber. The volumes of the first and second variable volume chambers are varied in a periodic and controller manner. The volumes of the first and second variable volume chambers while varied in a periodic manner, maintain the total volume of the two chambers as a constant volume. This causes the vapor phase of the substance to flow between the headspace of the sample vial, the sample loop and the variable volume chambers. As a result a sample of the equilibrated vapor phase of the substance passes through the sample loop without disturbance of the thermodynamic equilibrium between the vapor phase and the non-vapor phase of the substance. The aliquot of material in the sample loop is then analyzed using a gas chromatograph or other analytical instrument.

Alternative embodiments of the invention may be used to analyze samples which undergo time dependent or concentration dependent processes. Alternative embodiments may also be used to change the concentration of analytes or to add analytes to the material subject to analysis. Embodiments of the invention may also be used to carry out adsorption or desorption experiments. Exemplary embodiments of the invention may also include provisions for purging sample vapors from the systems to minimize the risk of cross contamination between samples.

BEST MODES FOR CARRYING OUT INVENTION

Figure 1:
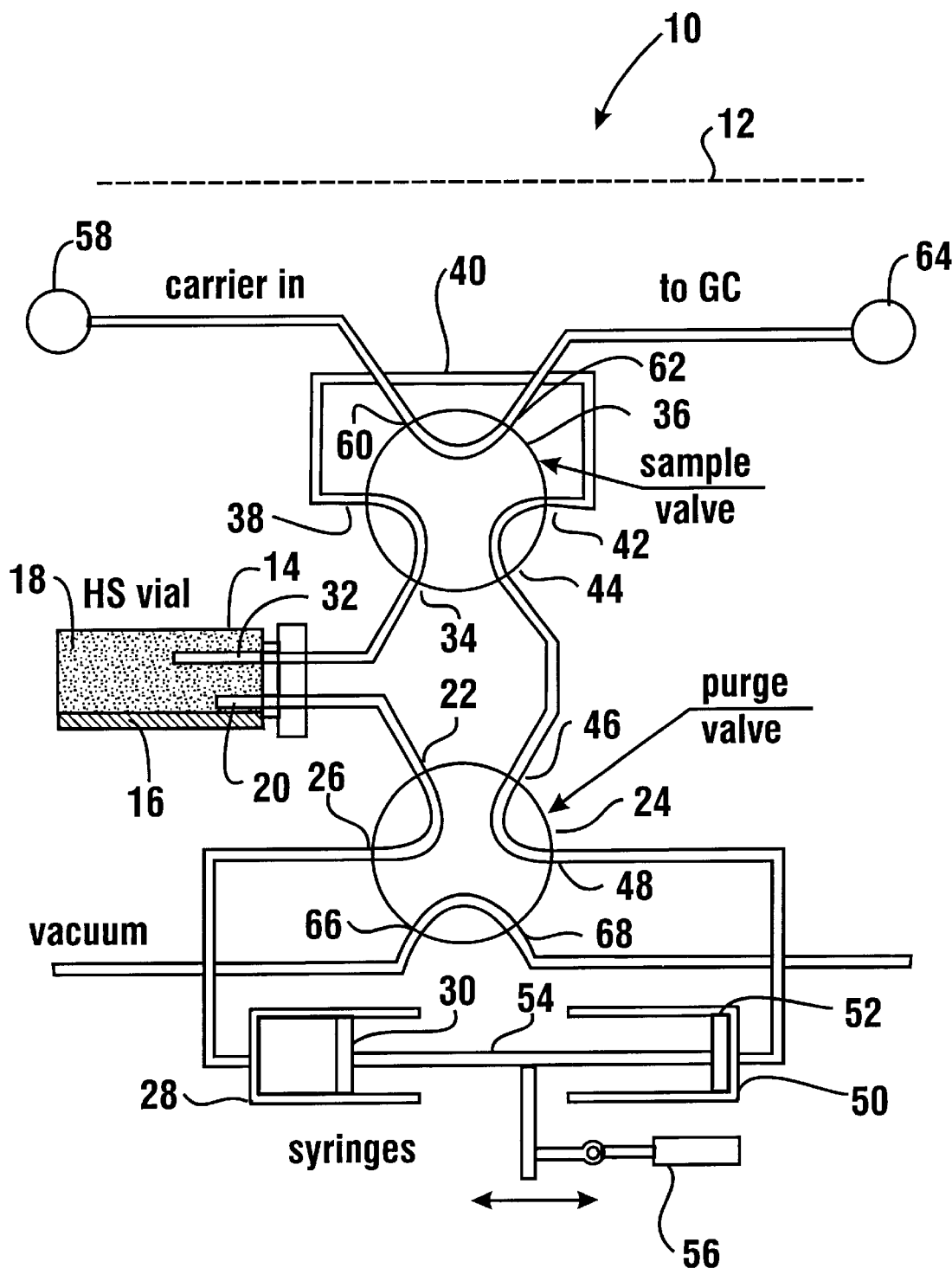
FIG. 1 is a schematic view of a first headspace instrument shown in a condition in which an equilibrated headspace sample is passed through a sample loop.

Referring now to the drawings and particularly to FIG. 1 there is shown therein a first embodiment of a headspace instrument of the present invention generally indicated 10. In the exemplary embodiment the headspace instrument is generally positioned within an equilibration chamber schematically indicated 12. The equilibration chamber is generally a chamber that maintains environmental conditions suitable for carrying out analysis of a vapor phase of a sample. This may include for example maintaining particular temperature conditions within the equilibration chamber. Alternatively or in addition it may include maintaining certain pressure or atmospheric conditions within the equilibration chamber. In the analysis of many samples the equilibration chamber is maintained at an elevated temperature above ambient to facilitate attaining of equilibrium between a vapor phase and a non-vapor phase of the sample.

The first instrument 10 is shown in connection with a headspace vial 14. Headspace vial 14 holds a substance which is subject to analysis. A non-vapor phase of the substance 16 is shown in a lower portion of a vial. The non-vapor phase of the substance may be a liquid or a solid phase of the substance being analyzed. The vapor phase of the substance 18 extends in a headspace in the vial above the non-vapor phase of the substance.

A first sample needle 20 extends into the vapor phase of the sample in the headspace of vial 14. In an exemplary embodiment first sample needle 20 extends through a resilient septum which bounds the headspace in the vial. This is done in the manner described in U.S. Pat. No. 5,441,700 the disclosure of which is incorporated herein by reference. First sample needle 20 is in fluid communication with a port 22 of a purge valve 24. Purge valve 24 is a six port valve which selectively connects adjacent ports of the valve depending on the valve condition. In the condition of the valve shown in FIG. 1, port 22 is in fluid communication through the valve with a port 26. Port 26 is in fluid connection with a first variable volume chamber 28. First variable volume chamber is bounded by a movable first piston 30.

A second sample needle 32 also extends in the vapor phase of the substance in the headspace of the vial. Second sample needle 32 is in fluid connection with a port 34 of a sample valve 36. Sample valve 36 in the exemplary embodiment is also a six port valve similar in construction to purge valve 24.

In the condition of sample valve 36 as shown in FIG. 1 port 34 is in fluid connection through the valve with a port 38. Port 38 is in fluid connection with a sample loop 40. Sample loop 40 is operative to hold and pass therethrough a vapor phase of the substance to be analyzed. Sample loop 40 is also in fluid connection with a port 42 of the valve 36. Port 42 in the condition of the valve 36 shown in FIG. 1, is in fluid connection through the valve with a port 44.

Port 44 of the sample valve 36 is in fluid connection with a port 46 of the purge valve 24. In the condition of the purge valve shown in FIG. 1 port 46 is in fluid connection through the purge valve with a port 48. Port 48 is in fluid connection with a second variable volume chamber 50. Second variable volume 50 is bounded by a movable second piston 52.

In an exemplary embodiment of the invention first variable volume chamber 28 and second variable volume chamber 50 are identical, as are respective pistons 30 and 52. First piston 30 is operatively connected to piston 52 through a connecting mechanism schematically indicated 54. Connecting mechanism 54 is operative to require piston 30 and piston 52 to move in coordinated relation. In the described embodiment the structure of the pistons and connecting mechanism is such that as the volume within the first variable volume chamber increases, the volume within the second variable volume chamber 50 decreases. Likewise as the volume within the second variable volume chamber increases, the volume of the first variable volume chamber 28 decreases. The structure of the exemplary embodiment is such that the total volume within chambers 28 and 50 remains a constant at all times. The connecting mechanism is selectively driven in a synchronized periodic fashion by a drive schematically indicated 56. In an exemplary embodiment of the invention syringes are used to define the first and second variable volume chambers. Plungers of the syringes are moved in coordinated relation using a pneumatic operator. However in other embodiments of the invention other variable volume chamber structures and drive mechanisms may be used.

In the condition of sample valve 36 shown in FIG. 1 a carrier gas source schematically indicated 58, is in operative connection with a port 60 of the sample valve. In the condition of the sample valve shown in FIG. 1 port 60 is in fluid connection through the valve with a port 62. Port 62 is in fluid communication with an analytical instrument such as a gas chromatograph schematically indicated 64. In the condition of the sample valve shown in FIG. 1 the carrier gas flows through the analytical instrument to clear the instrument of prior samples in preparation for delivery of a vapor sample thereto as later explained. As shown in FIG. 1 purge valve 24 includes ports 66 and 68. In the condition of the purge valve 24 shown in FIG. 1 ports 66 and 68 are in fluid communication. Each of ports 66 and 68 is in fluid communication with a vacuum source for purposes which are later explained.

In operation of the headspace instrument 10 the pistons 30, 52 are moved in reciprocating motion by the drive 56. An equilibrated vapor phase of the sample generated in the headspace of the vial is moved back and forth between the headspace, the sample loop and the first and second variable volume chambers. As the total volume of the headspace in the vial, the sample loop and the chambers 28, 50 remains a constant, the vapor phase of the sample reaches equilibrium with the non-vapor phase of the sample, and this equilibrated vapor phase extends in the sample loop 40.

Figure 2:
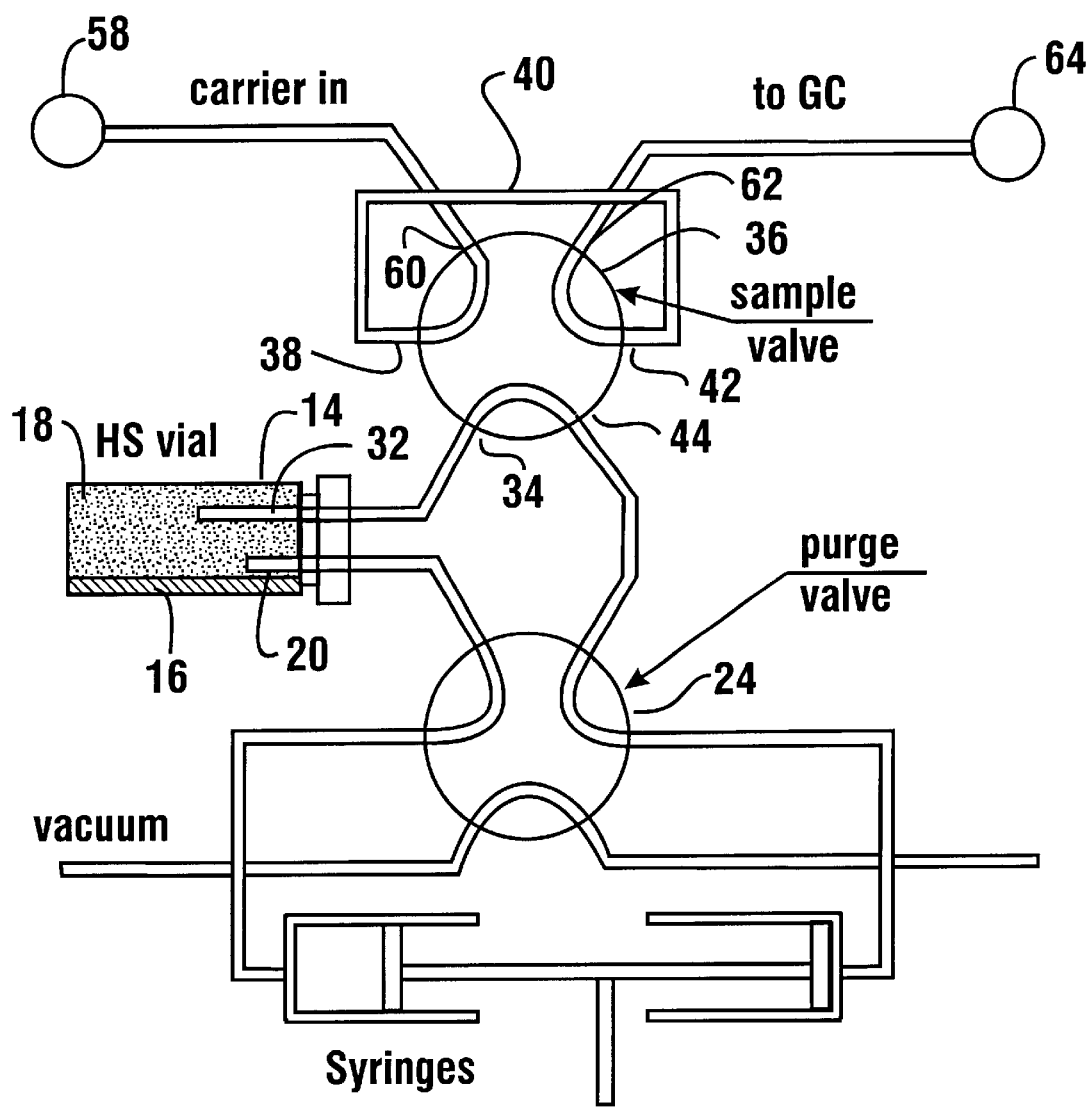
FIG. 2 is a further schematic view of the headspace instrument shown in FIG. 1 in a condition passing an aliquot of the vapor sample in the sample loop to an analytical instrument.

To deliver the equilibrated vapor phase of the sample to the analytical instrument the sample valve 36 is changed to the condition shown in FIG. 2. In this condition port 60 is placed in fluid communication with port 38 through the valve. As a result carrier gas from the carrier gas source 58 moves the vapor phase sample through the sample loop 40. The vapor phase sample passes through port 42 of the valve which is in fluid communication with port 62. The sample passes from port 62 and into the analytical instrument 64. In this condition of the valve ports 34 and 44 are placed in fluid communication to isolate the remainder of the system. Because the vapor phase of the sample passed through the sample loop 40 prior to changing the condition of the valve is in equilibrium with the non-vapor phase of the sample, the material passed from the sample loop to the analytical instrument is an aliquot of the sample material in the headspace taken in a manner which does not disturb the thermodynamic equilibrium between the vapor phase and the non-vapor phase of the substance being analyzed. As a result the sampling process does not affect the makeup of the sample which is a drawback associated with other sampling techniques.

Figure 3:
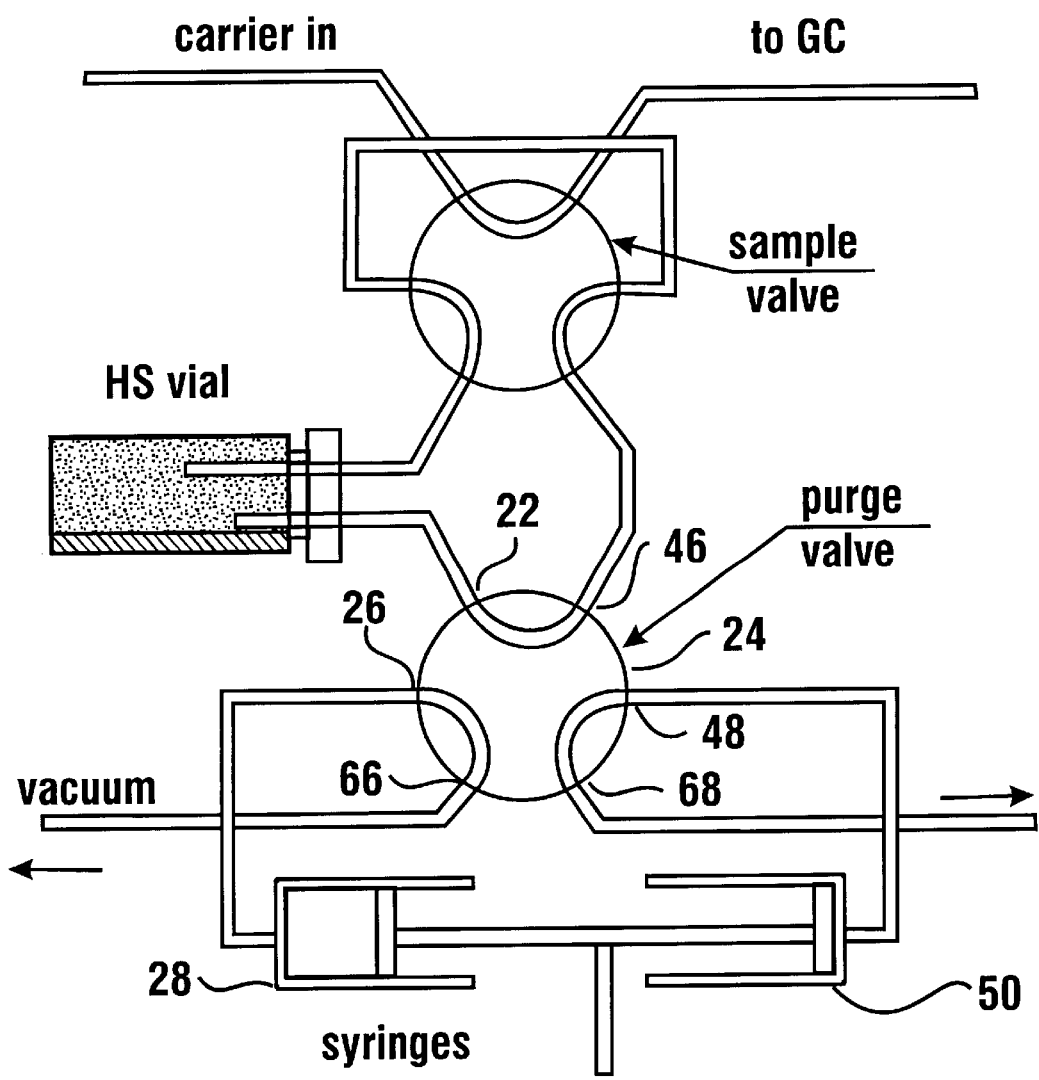
FIG. 3 is a further schematic view of the headspace instrument shown in FIG. 1 shown in a condition for removing contaminants from the instrument.

FIG. 3 represents the capabilities of the headspace instrument to reduce the risk of cross contamination between samples. After analysis of the sample the system requires cleansing to remove the residual analytes. Changing the purge valve 24 to the condition shown in FIG. 3 causes suction to be applied to each of chambers 28 and 50. The suction draws the residual analytes from the chambers. To determine if any residual amount is present the instrument can be operated to analyze the contents of the sample loop. If any analyte is determined to be present then the time during which the vacuum is applied may be increased. This minimizes the risk that any residual amount of material from prior samples remains in the instrument prior to analysis of a subsequent sample.

Figure 4:
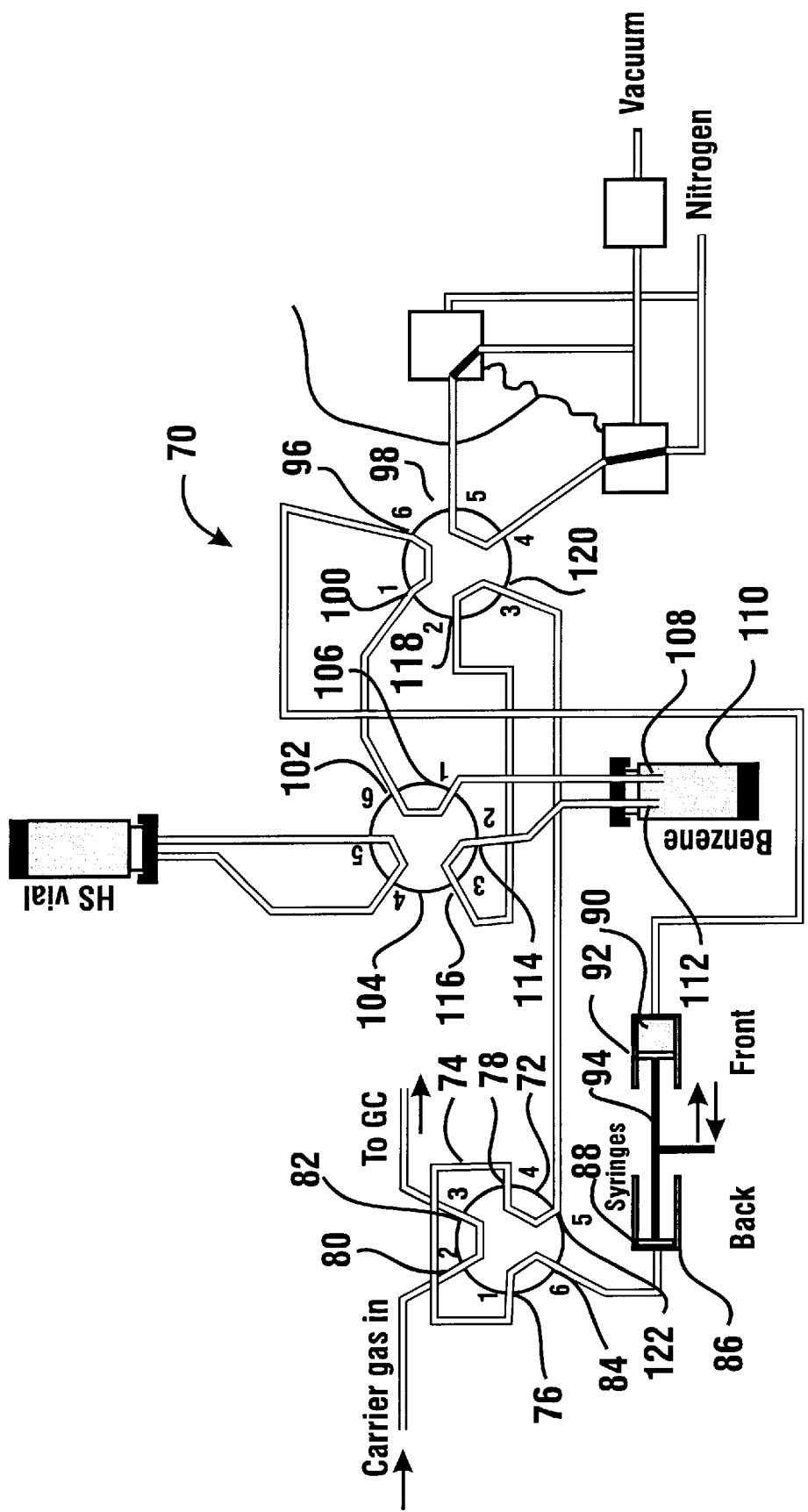
FIG. 4 is a schematic view of a second embodiment of a headspace instrument of the present invention shown in the condition in which an equilibrated headspace sample from a sample vial is passed through a sample loop.
Figure 5:
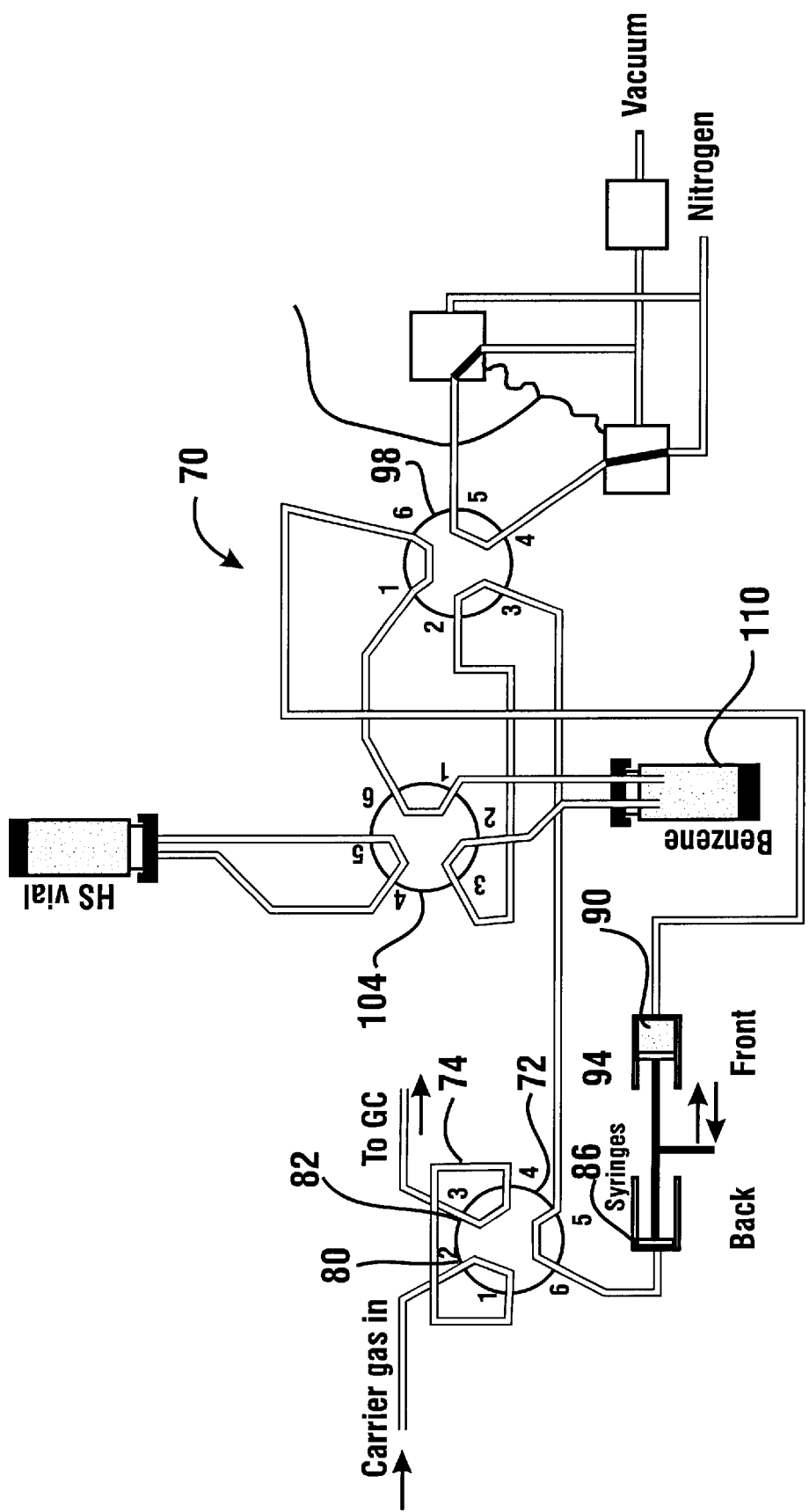
FIG. 5 is a schematic view of the alternative headspace instruments shown in FIG. 4 in a condition passing the vapor sample in the sample loop to an analytical instrument.

FIGS. 4–8 schematically show a second headspace instrument 70. Instrument 70 is particularly adapted for carrying out concentration dependent processes and adsorption and desorption experiments. Instrument 70 includes a sample valve 72 which is a six port valve similar to sample valve 24. A sample loop 74 is connected between ports 76 and 78 of valve 72 in a manner similar to that previously described. A port 80 of valve 72 is connected to a source of carrier gas. Port 82 is connected to an analytical instrument. As represented in FIG. 5 the condition of sample valve 72 may be selectively changed such that the material in the sample loop 74 is delivered to an analytical instrument such as a gas chromatograph which is in fluid connection with port 82.

Returning to the description of the system in FIG. 4, a port 84 of sample valve 72 is connected to a first variable volume chamber 86. First variable volume chamber 86 is bounded by a movable first piston 88 in a manner similar to that previously discussed. A second variable volume chamber 90 is bounded by a movable second piston 92. First and second pistons 88 and 92 are connected by a connecting mechanism 94 and are moved in coordination by a drive (not shown). Similar to the first instrument the configuration of the first and second chambers provides a total volume for both chambers which equals a constant value.

Second variable volume chamber is in fluid connection with a port 96 on a second valve 98. Second valve 98 is a six port valve similar to the sample valve 72 as shown. In the condition of valve 98 shown, port 96 is in fluid connection through the valve with a port 100. Port 100 is in fluid connection with a port 102 on a vial switching valve 104. In the condition of valve 104 shown in FIG. 4, port 102 is in fluid connection through the valve with a port 106. Port 106 is fluidly connected to a first sample needle 108 which extends in the headspace in a sample vial 110.

A second sample needle 112 also extends in the headspace of sample vial 110 sample needle 112 is in fluid connection with a port 114 of vial switching valve 104. In the condition of valve 104 shown in FIG. 4 port 114 is in fluid connection through the valve with a port 116. Port 116 is in fluid connection with a port 118 on valve 98. In the condition of valve 98 shown in FIG. 4, port 118 is in fluid connection with a port 120. Port 120 is fluidly connected to a port 122 on sample valve 172 which in the condition of the valve shown is connected to the sample loop 74.

As can be appreciated from FIG. 4, in the condition of the valve 104 shown a vapor phase of a substance in the headspace of sample vial 110 flows through the first and second variable volume chambers 86 and 90 and the sample loop 74. In this condition of valves 98 and 104 when the sample valve 72 is changed to the condition shown in FIG. 5 an equilibrated sample of the headspace vapor from vial 110 is delivered from port 82 of sample valve 72 to the analytical instrument.

Figure 6:
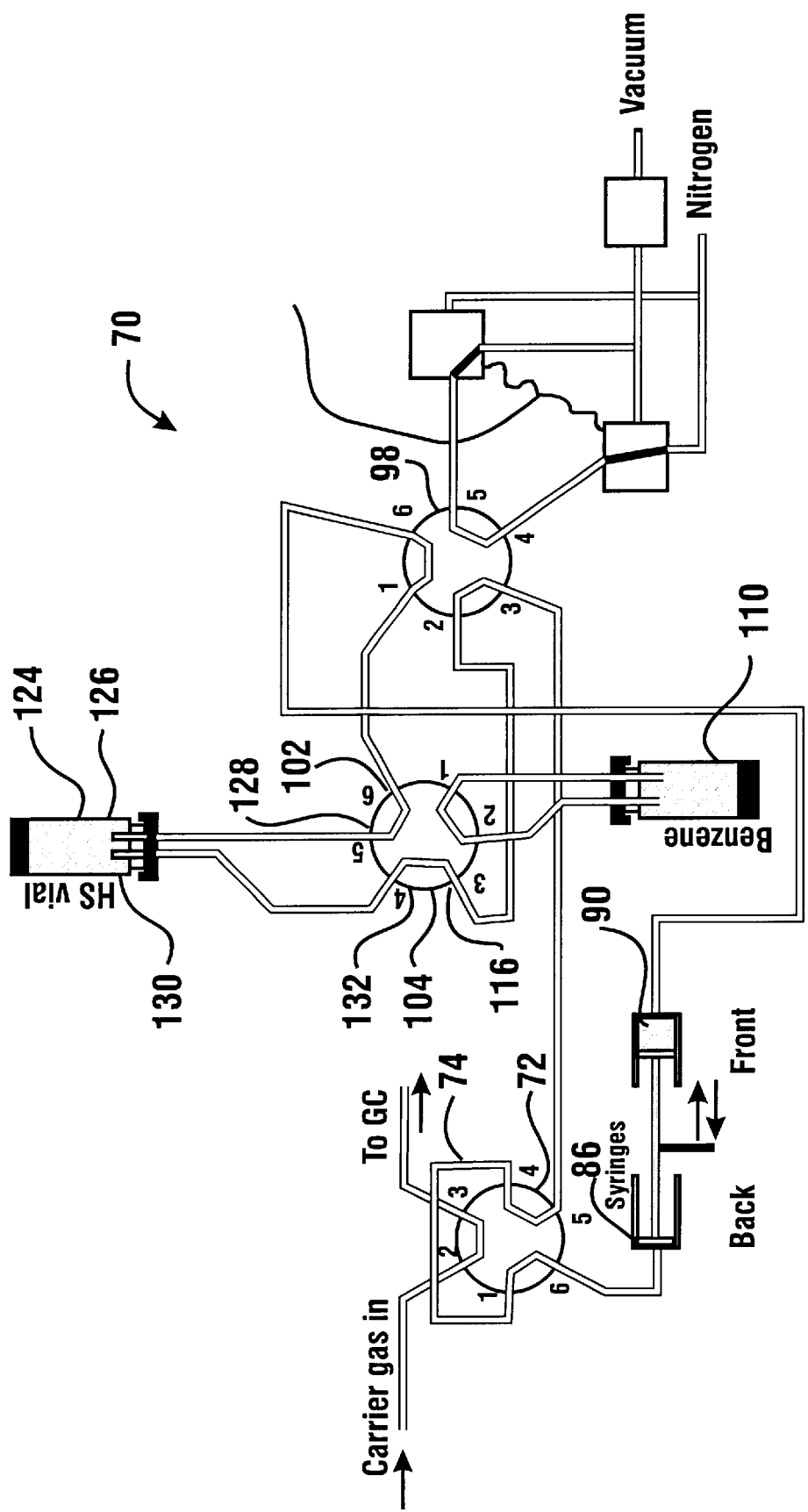
FIG. 6 is a further schematic view of the alternative headspace instrument shown in FIG. 4, passing an equilibrated vapor sample from a headspace vial through a sample loop.

As schematically shown in FIG. 6, the sample loop 74 may alternatively include an equilibrated sample of the headspace vapor from a headspace vial 124. It should be understood that headspace vial 124 is shown in inverted position in FIG. 6. Headspace vial 124 includes a sample needle 126 which extends in the headspace of the vial. Sample needle 126 is in fluid connection with a port 128 of vial switching valve 104. A sample needle 130 which also extends in the headspace of vial 124, is in fluid connection with a port 132 of valve 104.

In the condition of valve 104 shown in FIG. 6, port 102 is fluidly connected through valve 104 to port 128. Port 132 is fluidly connected through the valve to port 116. As a result port 128 is fluidly connected to valve 98 in the condition shown to second variable volume chamber 90. Similarly port 132 is connected through valve 98 to sample loop 74 and the first variable volume chamber 86. In this condition of the valves of the instrument, the sample loop 74 is filled with an equilibrated sample of the headspace vapor of the material in headspace vial 124. Changing the condition of sample valve 72 from the condition shown in FIG. 6 to the condition shown in FIG. 5, thus results in delivering headspace vapor from vial 124 to the analytical instrument.

Figure 7:
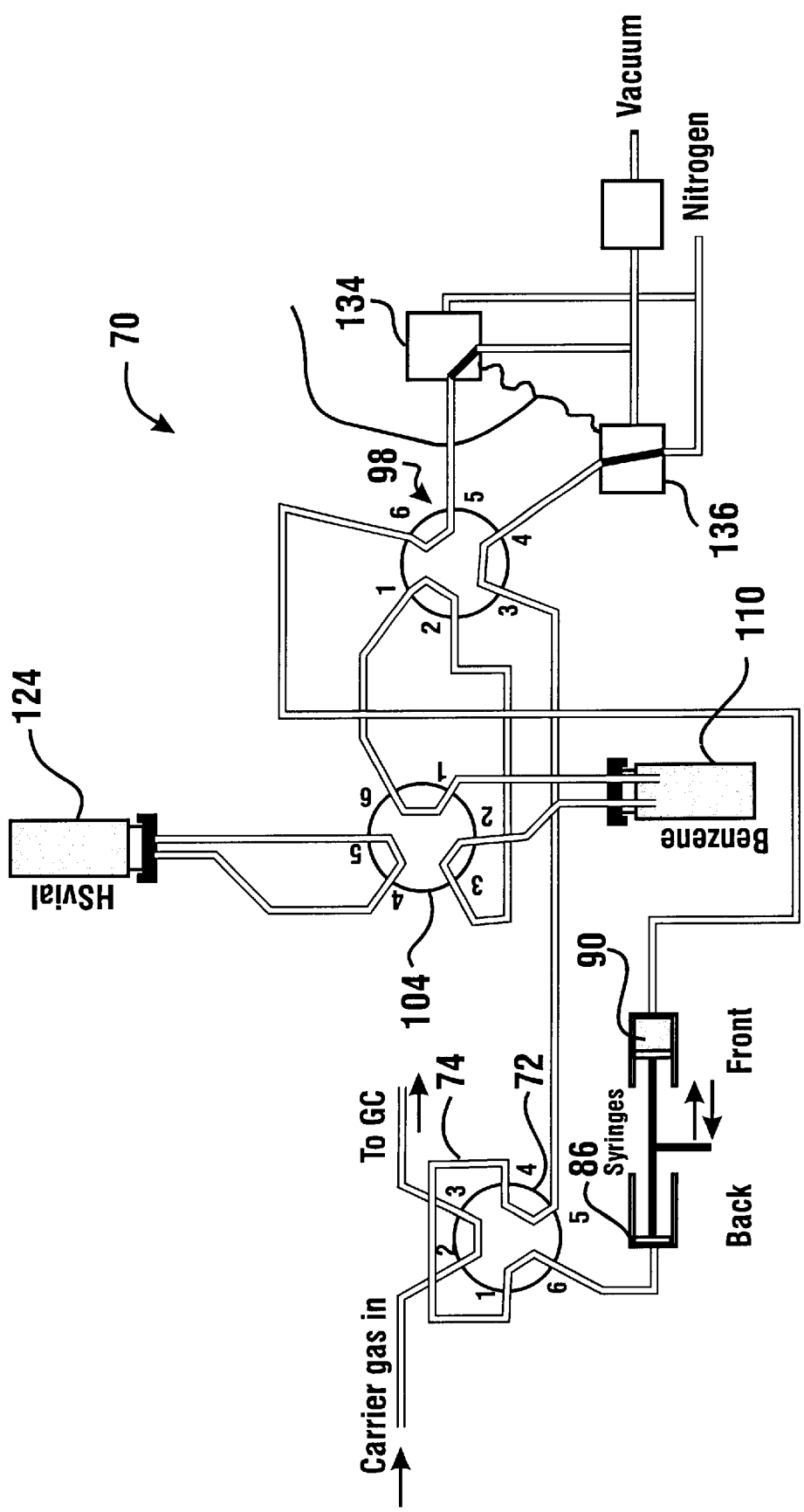
FIG. 7 is a schematic view of the alternative headspace instrument shown in a condition removing contaminants from the instrument.
Figure 8:
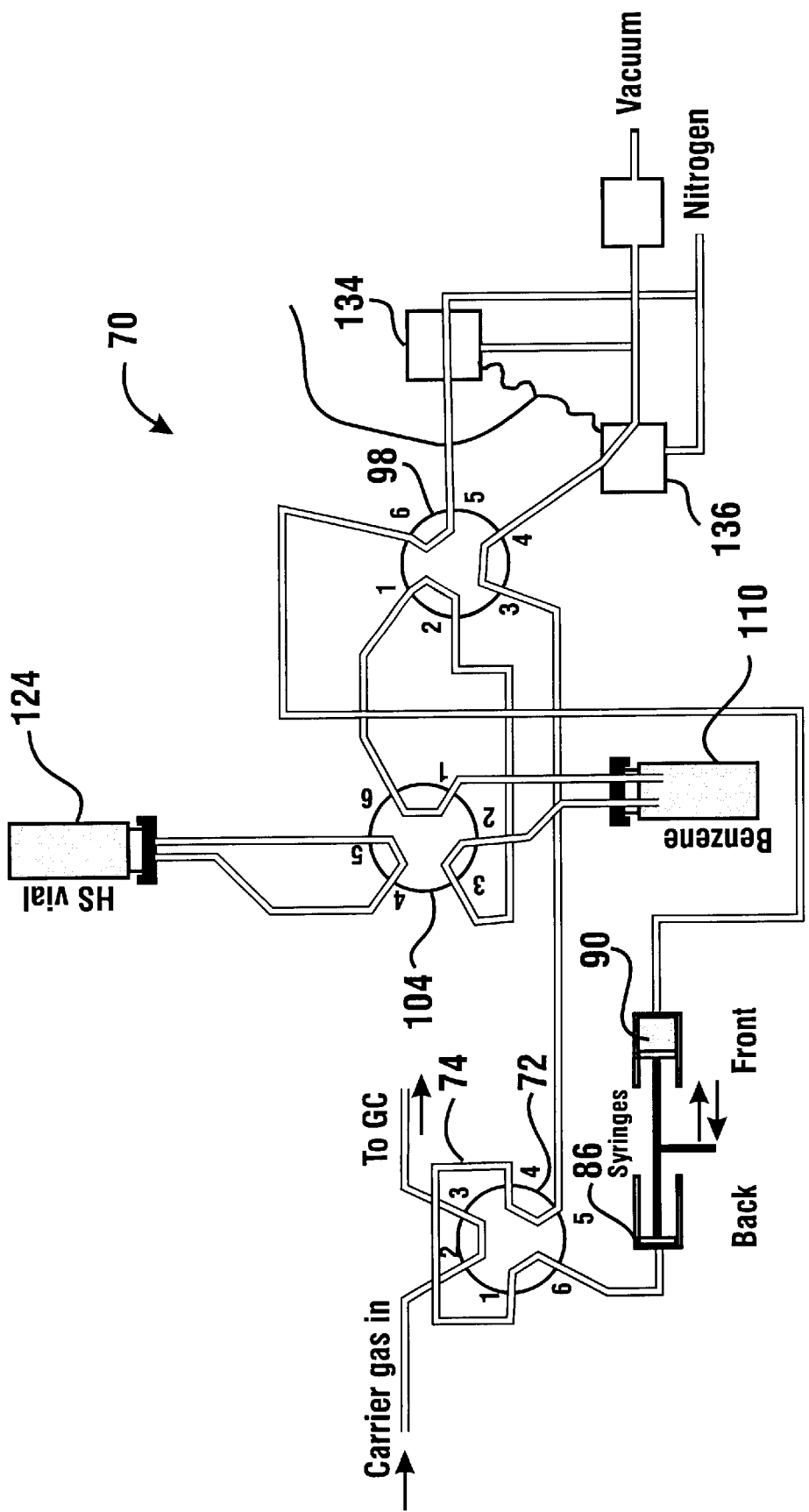
FIG. 8 is a schematic view of the alternative headspace instrument shown in an alternative condition for removing contaminants from the instrument.

FIGS. 7 and 8 demonstrate the capabilities of the headspace apparatus 70 to remove residual analytes from the system. This reduces the possibility of cross contamination between samples. Placing valve 98 in the condition shown in FIG. 7 results in second variable volume chamber 90 being placed under suction. This is accomplished through a three-way valve 134. In the condition of valve 134 shown in FIG. 7 a vacuum source is applied through valve 98 to chamber 90. At the same time a nitrogen source is connected through valve 98 to the sample valve 92, the sample loop 74 and the first variable volume chamber 86. The nitrogen source is connected through valve 136.

As shown schematically in FIG. 8 changing the respective conditions of valves 134 and 136 results in the application of the vacuum to the first variable volume chamber 86 and sample loop 74. In this condition of the valves the nitrogen source is applied to second variable volume chamber 90. The application of suction and the nitrogen source serves to remove residual analytes from the system and to reduce the risk of contamination between samples.

The second headspace apparatus is particularly well adopted for carrying out sampling of substances involved in concentration dependent processes because each of the sample vial and headspace vial may be selectively connected to the sample loop. Analytes may also be transferred from one vial to the other. Such features are useful in changing the concentration by extraction and/or transferring analytes from one vial to another. The capabilities of the exemplary instrument 70 is also useful in the conduct of adsorption or desorption.

For example the headspace vial 124 may be loaded with a known amount of adsorbent or catalyst. The analyte of interest maybe placed in the sample vial. The headspace of the sample vial is equilibrated with the sample loop. The material in the sample loop is then transferred to the headspace of the headspace vial 124 by changing the condition of the vial switching valve 124. After adsorption equilibrium is achieved. The amount adsorbed into the adsorbent or catalyst maybe determined as a difference from the amount transferred. This application also offers the possibility to transfer a mixture of different analytes from a sample vial simultaneously and has the separate capability to study competitive adsorption at any desirable temperature. Interaction energies of certain analytes with particular adsorbent or catalysts maybe studied as well for surface heterogeneity.

As can be appreciated the preferred form of headspace instrument 70 is maintained with its components within an equilibration chamber. This enables the components of the system to be at the desired temperatures and pressures for avoiding undesirable sample condensation or other conditions which may adversely impact the sensitivity of the headspace instrument.

It should be understood that the headspace instruments described herein are exemplary and the principles of the invention may be applied to other headspace instruments and devices. It should be further understood while the exemplary embodiments have been discussed in connection with using a gas chromatograph as an analytical instrument, other types of analytical instruments may also be used. These may include for example, spectrophotometers, semiconductor aroma sensors, or other sensor types which may receive equilibrated vapor samples from the sample loop for which may operate to analyze constituents or properties of vapor within the sample loop.

Thus the headspace instrument and methods of the present invention achieves the above-stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are for descriptive purposes and are intended to be broadly construed. Moreover the descriptions and illustrations herein are by way of examples and the invention is not limited to the detail shown and described. Further, in the following claims any feature described as a means for performing a function shall be construed as encompassing any means known to those skilled in the art to be capable of performing the recited function, and shall not be deemed limited to the particular means shown in the foregoing description as performing the recited function or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations and relationships are set forth in the appended claims.

We claim:

1. A headspace instrument comprising:

a vial, wherein the vial includes a headspace, wherein when a substance to be analyzed is placed within the vial, the headspace is operative to hold a portion of the vapor phase of the substance, and wherein the vial includes a first sample needle and a second sample needle, wherein both the first sample needle and the second sample needle are in fluid communication with the headspace of the vial;

a first chamber and a second chamber, wherein the first chamber includes a first variable volume, and wherein the second chamber includes a second variable volume, wherein the first chamber and the second chamber are operative responsive to at least one drive mechanism to simultaneously increase the first variable volume of the first chamber and decrease the second variable volume of the second chamber, and wherein the first chamber and the second chamber are further operative responsive to the at least one drive mechanism to simultaneously decrease the first variable volume of the first chamber and increase the second variable volume of the second chamber;

a purge valve, wherein the first sample needle, the first chamber, and the second chamber are individually in fluid communication with the purge valve;

a sample loop, wherein the sample loop includes a first end and a second end;

a sample valve, wherein the second sample needle, the first end of the sample loop, the second end of the sample loop, and the purge valve are individually in fluid communication with the sample valve; and wherein when the purge valve is in a first condition and the sample valve is in a first condition, the purge valve and the sample valve are operative to place the first sample needle in fluid communication with the first chamber, the second sample needle in fluid communication with the first end of the sample loop, and the second end of the sample loop in fluid communication with second chamber, whereby the vial and the sample loop are placed in fluid communication in series between the first chamber and the second chamber.

2. The headspace sampling apparatus according to claim 1, further comprising a connection member, wherein the first chamber is bound by a first piston, wherein the second chamber is bound by a second piston, wherein the connection member is in operative connection between the first piston and the second piston, wherein the connection member is operative to synchronize the movements of the first piston and the second piston.

3. The headspace instrument according to claim 1, further comprising the drive mechanism in operative connection between the first chamber and the second chamber, wherein the drive mechanism is operative to simultaneously decrease the first variable volume by a first amount of volume and increase the second variable volume by a second amount of volume that corresponds to the first amount of volume, wherein as the first and second variable volumes change, a portion of the vapor phase of the substance is urged to flow from the headspace of the vial to the sample loop.

4. The headspace instrument according to claim 3, wherein the first amount of volume is about equal to the second amount of volume.

5. The headspace instrument according to claim 3, wherein the first chamber is bound by a first piston and the second chamber is bound by a second piston, wherein the drive mechanism is selectively operative to move the first piston and the second piston in a reciprocating motion.

6. The headspace sampling apparatus according to claim 5, wherein the total volume of the headspace, the sample loop, the first chamber and the second chamber remains generally constant, whereby thermodynamic equilibrium is maintained in the headspace of the vial as the vapor phase of the substance flows through the sample loop.

7. The headspace instrument according to claim 3, further comprising:
an analytical instrument;
a carrier gas source, wherein the sample valve is in fluid communication with the carrier gas and the analytical instrument; and
wherein when the sample valve is in a first condition, the sample valve is operative to place the carrier gas source in fluid communication with the analytical instrument, wherein the sample valve is operative to direct a carrier gas from the carrier gas supply to flow to the analytical instrument, whereby the analytical instrument maybe purged of a prior sample.

8. The headspace instrument according to claim 7, wherein when the sample valve is in a second condition, the sample valve is operative to place the sample loop in fluid communication between the carrier gas supply and the analytical instrument, wherein the carrier gas from the carrier gas supply is operative to flow through the sample loop and urge the portion of the vapor phase of the substance in the sample loop to flow to the analytical instrument.

9. The headspace instrument according to claim 8, further comprising:
a vacuum source, wherein the purge valve is in fluid communication with the vacuum source; and
wherein when the purge valve is in a second condition the purge valve is operative to place both the first chamber and the second chamber in fluid communication with the vacuum source, wherein the vacuum source is operative to urge residual substances out of the first chamber and the second chamber.

10. The head space instrument according to claim 8 comprising:
a second vial;
a vial switching valve in fluid communication with the sample needles of the first vial and second vial, wherein the vial switching valve is operative to selectively place either the sample needles of the first vial or the sample needles of the second vial in fluid communication with the purge valve and the sample valve.

11. The headspace instrument according to claim 10, further comprising:
a vacuum source;
a purging gas source, wherein the purge valve is operative to selectively place the first and second chambers in fluid communication with the vacuum source and the purging gas source, whereby each of the chambers can be alternatingly filled with a purge gas from the purging gas source and suctioned out with the vacuum source.

12. The headspace sampling apparatus according to claim 7, wherein the analytical instrument is a gas chromatograph.

13. The headspace sampling apparatus according to claim 1, wherein the vial is in operative connection with an equilibration chamber, wherein the equilibration chamber is operative to generally maintain an equilibrium between the vapor phase of the material and a non vapor phase of the material being analyzed.

14. The headspace sampling apparatus according to claim 13, wherein the equilibration chamber is operative to maintain the vial at an elevated temperature.

15. The headspace sampling apparatus according to claim 1, wherein the first sample needle and the second sample needle extend through a resilient septum which bounds the headspace of the vial.

16. A method of using a headspace sampling instrument comprising:
loading a first vial with a known amount of a first substance;
loading a second vial with a second substance;
generating a vapor phase of the second substance in a headspace of the second vial;
urging a portion of the vapor phase of the second substance to flow from the headspace of the second vial into a sample loop, including simultaneously increasing the volume of a first variable volume chamber and decreasing the volume of a second variable volume chamber, wherein the headspace of the second vial and the sample loop are in fluid communication between the first variable volume chamber and the second variable volume chamber, and including maintaining a first total volume of the headspace of the second vial, the sample loop, the first variable volume chamber, and the second variable volume chamber at a generally constant level;
placing the sample loop in fluid communication with the first vial; and
urging the portion of the vapor phase of the second substance to flow from the sample loop into a headspace of the first vial, including simultaneously decreasing the volume of the first variable volume chamber and increasing the volume of the second variable volume chamber, wherein the headspace of the first vial and the sample loop are in fluid communication between the first variable volume chamber and the second variable volume chamber, and maintaining a second total volume of the headspace of the first vial, the sample loop, the first variable volume chamber, and the second variable volume chamber at a generally constant level.

17. The method of using the headspace sampling instrument according to claim 16, further comprising enabling the vapor phase of the second substance to interact with the first substance.

18. The method of using the headspace sampling instrument according to claim 16, further comprising:
  measuring the first substance to determine a new amount; and
  comparing the known amount of the first substance to the new amount.

19. The method of using the headspace sampling instrument according to claim 16, further comprising maintaining the first vial at a generally constant temperature.

20. The method of using the headspace sampling instrument according to claim 16, further comprising:
  purging residual gases from the sample loop and the variable volume chambers;
  placing the sample loop in fluid communication with an analytical instrument; and
  determining the concentration of residual gases.

21. A headspace instrument comprising:
  a first vial, wherein the first vial is operative to include a first substance therein;
  a second vial, wherein the second vial includes a headspace, wherein the second vial is operative to include a second substance therein, wherein the headspace of the second vial is operative to include a vapor phase of the second substance;
  a sample loop;
  a first chamber;
  a second chamber;
  at least one drive mechanism; and
  at least one valve, wherein the at least one valve is operative to place the sample loop and the second vial in fluid communication between the first and second chambers, wherein the first chamber and the second chamber are operative responsive to the at least one drive mechanism to simultaneously increase a volume of the first chamber and decrease a volume of the second chamber, thereby urging a portion of the vapor phase of the second substance to flow from the headspace of the second vial into the sample loop, and wherein the at least one valve is operative to place the sample loop and the first vial in fluid communication between the first chamber and the second chamber, wherein the first chamber and the second chamber are operative responsive to the at least one drive mechanism to simultaneously decrease the volume of the first chamber and increase the volume of the second chamber, thereby urging a portion of the vapor phase of the second substance to flow from the sample loop to the first vial.

22. The instrument according to claim 21, wherein the drive mechanism is operative to maintain the sum of the volumes of the first chamber and the second chamber at a constant amount while causing the volumes of the first chamber and the second chamber to change.

23. The instrument according to claim 22 wherein the second vial includes two openings in fluid communication with the headspace, wherein the sample loop includes two ends, wherein the at least one valve is operative to connect the two openings of the second vial and the two ends of the sample loop in series between the first chamber and the second chamber.

24. The instrument according to claim 23 wherein the first vial includes two openings, wherein the at least one valve is operative to connect the two openings of the first vial and the two ends of the sample loop in series between the first chamber and the second chamber.

* * * * *